United States Patent [19]

Kerr et al.

[11] Patent Number: 4,643,899

[45] Date of Patent: Feb. 17, 1987

[54] MICROORGANISM HAVING CHARACTERISTICS OF AN ARTHROBACTER CAPABLE OF DEGRADING PEANUT HULL LIGNIN

[75] Inventors: Thomas J. Kerr, Athens, Ga.; Robert D. Kerr, Salem, Ala.

[73] Assignee: Georgia Research Foundation, Athens, Ga.

[21] Appl. No.: 551,220

[22] Filed: Nov. 14, 1983

[51] Int. Cl.⁴ .......................... D21C 1/00; C12R 1/06; A23C 9/12; A23L 1/28; C12N 1/20; C07G 17/00

[52] U.S. Cl. .......................................... 426/2; 426/44; 426/46; 426/49; 426/54; 426/61; 435/253; 435/267; 435/277; 435/830

[58] Field of Search ............... 435/262, 267, 277, 830, 435/253; 426/44, 46, 2, 49, 54

[56] References Cited

PUBLICATIONS

Kerr, T. J. et al., "Isolation of a Bacterium Capable of Degrading Peanut Hull Lignin" Applied & Environmental Microbiology 46(5) 1201-6, Nov. 1983.

Cartwright et al., "Enzymic Lignin, Its Release & Utilization by Bacteria" Microbios. 8(29) 7-14, 1973.

Kerr, T. J. et al., "SEM Study of the Biodegradation of Peanut Hulls" Abstract #K98, Abstracts Annual Mtg. Am. Soc. Microbiol. 83(0), May 6-11, 1983, New Orleans, La.

Kerr, T. J. et al., "Biological Conversion of Peanut Hulls to Cattle Feed", Abstract #K218, Abstracts Annual Mtg. Am. Soc. Microbiol. 83(0), Mar. 6-11, 1983, New Orleans, La.

Barton et al., "Treating Peanut Hulls to Improve Digestibility for Ruminants" J. Animal Science 38(4) 860-864, 1974.

*Primary Examiner*—Thomas G. Wiseman
*Assistant Examiner*—Robin Lyn Teskin
*Attorney, Agent, or Firm*—Oblon, Fisher, Spivak, McClelland & Maier

[57] ABSTRACT

A newly discoverd microorganism having characteristics of an Arthrobacter and having the ability to utilize peanut hull lignin as a sole source of carbon is disclosed. Peanut hulls have a higher lignin content than hardwoods and softwoods. The newly discovered microorganism makes the biodegradation of peanut hulls and other similar lignin containing biological waste products commercially feasible. Specifically, a process for converting peanut hulls and other similar lignin containing biological waste products to animal feed is disclosed.

19 Claims, No Drawings

MICROORGANISM HAVING CHARACTERISTICS OF AN ARTHROBACTER CAPABLE OF DEGRADING PEANUT HULL LIGNIN

BACKGROUND AND SUMMARY OF INVENTION

During the part few years, the role of microorganisms in the decomposition of lignin and lignocellulosic plant materials has been studied. Wood-rot fungi have been considered to be the primary decomposers of lignin in nature. However, the ability of several strains of microorganisms to degrade chemically isolated lignin preparations as well as radiolabelled natural and synthetic lignins has been established.

Odier et al. (Odier, E., G. Janin, and B. Monties, Appl. Environ, Microbiol. 41:377–341, 1981) reported the isolation of eleven gram negative bacteria, identified as Pseudomonas, Xanthomonas, and Acinetobacter, that were capable of assimilating poplar dioxane lignin without a co-substrate. Several Nocardia strains have been shown to decompose radiolabelled natural and synthetic lignins and to utilize lignin as a carbon source (Gradziel, K., K. Haider, J. Kochmanska, E. Malarczyk, and J. Trojanowski, Acta Microbiol. Pol. 27:103–109, 1978; Haider, K., J. Trojanowski, and V. Sundman, Arch. Microbiol. 119:103–106, 1978; Trojanowski, J., K. Haider, and V. Sundman, Arch. Microbiol. 114:149–153, 1977). A strain of Bacillus and several strains of Streptomyces have been shown to degrade radiolabelled natural lignins (Crawford, D. L., Appl. Environ. Microbiol. 35:1041–1045, 1978; Crawford, D. L., M. J. Barder, A. L. Pometto, III and R. L. Crawford, Arch. Microbiol. 131:140–145, 1982; Crawford, D. L. and J. B. Sutherland, Dev. Ind. Microbiol. 20:143–151, 1979; Phelan, M. B., D. L. Crawford and A. L. Pometto, III, Can. J. Microbiol. 25:1270–1276, 1979; Robinson, L. E. and R. L. Crawford, FEMS Microbiol. Lett. 4:301–302, 1978; Sutherland, J. B., R. A. Blanchette, D. L. Crawford and A. L. Pometto, III, Curr. Microbiol. 2:123–126, 1979). Cartwright and Holdom (Cartwright, N. J. and K. S. Holdom, Microbios 8:7–14, 1973) isolated an Arthrobacter capable of utilizing enzymic lignin (lignin released by *Cellulomonas subalbus* from birch) as a sole carbon source which is the only prior reported Arthrobacter capable of degrading lignin.

Peanut hulls contain more lignin (approximately 32%) than most hardwoods and softwoods and they are very resistant to biodegradation (Kerr, et al. unpublished data). The present invention discloses the isolation of forty-two strains of microorganisms capable of degrading and assimilating peanut hull lignin. Four types of lignin preparations were chemically isolated from peanut hulls. Of the forty-two isolates, only one (KB-1—also referred to as K-7), tentatively identified as an Arthrobacter, was capable of utilizing all four lignin preparations as a sole source of carbon. This microorganism also has the ability to degrade specifically $^{14}C$-labelled natural lignin and $^{14}C$-labelled Kraft lignin.

By utilizing four types of lignins isolated from peanut hulls in addition to water extracted hulls, the present invention discloses forty-two microorganism isolates capable of using such lignins and water extracted hulls as sole carbon and energy sources. Only one microorganism, (KB-1), of the forty-two isolates was capable of growing on all four such lignins as well as water extracted peanut hulls. The present invention discloses that the preferred microorganism (KB-1) utilizes cellulose in addition to lignin, good growth of KB-1 was obtained using lignin preparations with no added carbohydrates or polysaccharides.

The tentative identification of the preferred microorganism (KB-1)—as a species of the genus Arthrobacter is based on its pleomorphic characteristics, even though they appear to be reversed. Usually, Arthrobacter species are isolated as cocci and when put into fresh media such species change to a rod shaped morphology, then back to cocci in older media. The microorganism KB-1 was isolated as a rod and grows as a rod on solid media, only changing to the coccoid form in liquid media. In addition to this pleomorphism, results from the biochemical tests generally match those described for Arthrobacter species in Bergey's manual (Buchanan, R. E. and N. E. Gibbons, Bergey's Manual of Determinative Bacteriology, 8th ed., 1974).

The only prior report of a lignolytic Arthrobacter referred to above was by Cartwright and Holdom (Cartwright, N. J. and K. S. Holdom, Microbios, 8:7–14, 1973) who reported the isolation and characterization of an Arthrobacter that utilized enzymic lignin (from birch—wood lignin) as a sole carbon source. Because Cartwright and Holdom failed to isolate a number of different organisms capable of growing on this enzymic lignin, they concluded that microorganisms such as Arthrobacter species as a whole have no major role in the degradation of lignin as it occurs in nature. Since peanut hulls contain significantly more lignin (approximately 32% lignin) than hardwoods and softwoods such as birch and in light of the conclusion of Cartwright and Holdon (Cartwright, N. J. and K. S. Holdom, Microbios, 8:7–14, 1973) the lignolytic Arthrobacter of Cartwright and Holdon is unrelated to the present invention. Moreover, the lignolytic Arthrobacter of Cartwright and Holdom was not reported to be capable of and would not be expected to utilize peanut hull lignin.

Another test of a microorganism's ability to degrade natural lignin is the use of specifically labelled $^{14}C$-(lignin)-lignocelluloses in biodegradation studies (Sarkanen, K. V. and C. H. Ludwig, Lignins: Occurrence, Formation, Structure and Reactions, Wiley Interscience, New York, 1971). The microorganism, KB-1, demonstrated the ability to significantly degrade the lignin fraction of the cordgrass, *S. alterniflora*. Thus, this bacterium was capable of degrading 4 lignin preparations from peanut hulls, Kraft lignin from *Pinus elliottii*, and natural lignin of the lignocellulose fraction from Spartina. The wide array of lignin substrates degradable by the microorganism KB-1 indicates the versitility of the lignolytic capabilities of this microorganism.

Approximately 1.6 million tons of peanuts are produced in the United States of America every year. Peanut hulls account for a quarter of this weight, or approximately 400,000 tons. Prior to the present invention, a commercial use for such amount of peanut hulls has not been disclosed. Peanut hulls continue to accumulate at shelling plants, particularly in the Southeastern United States of America where approximately 60% of the peanuts produced in the United States of America are grown. Natural rates of biodegradation of peanut hulls are very slow, although supplementation of hulls with $NH_4NO_3$ can significantly increase degradation rates.

A number of researchers have tested peanut hulls as both partial rations and as roughage substitute for cattle.

Utley et al. (Utley, P. R., R. S. Lowrey, and W. C. McCormick, J. Anim. Sci. 31:257, 1970) reported that peanut hulls were equal in roughage value to coastal Bermuda grass pellets or the cob and shuck fraction of ground snapped corn when added as 20% of a steer finishing diet. Utley et al. (Utley, P. R., R. E. Hellwig, J. L. Butler and W. C. McCormick, J. Anim. Sci. 37:603–611, 1973) also reported that cattle fed ground or pelleted peanut hulls developed an unusually high number of liver abscesses which suggested that only unground peanut hulls be added to feed as a roughage material. Using only unground hulls makes the use of peanut hulls as a roughage for cattle uneconomical because of the low density of unground hulls (5–6 lbs/cubic foot) and the high cost of transportation.

Since the turn of the century, attemps have been made to convert agricultural waste products into commercially valuable animal feed. A number of different chemical treatments have been used to increase digestibility of various agricultural wastes such as cotton seed hulls, sawdust, bark, and corn cobs (Capper, B. S., D. J. Morgan and W. H. Parr, Trop. Sci. 19:73–87, 1977). Chemical treatment to improve ruminant digestibility of peanut hulls has been reported by Barton et al. (Barton, F. E., H. E. Amos, W. W. Albrecht and D. Burdick, J. Anim. Sci 38:860–864, 1974). Treatment of hulls with a 1.82N solution of calcium hypochlorite increased their digestibility from 25% to 40%. Treatment with a variety of other chemicals such as sodium hydroxide actually decreased digestibility of hulls (Goering, H. K. and P. J. Van Soest, Trop. Sci. 19:73–87, 1977 and Barton, F. E., H. E. Amos, W. W. Albrecht and D. Burdick, J. Amin. Sci 38:860–864, 1974). Several chemical treatments at elevated temperatures have been used to disrupt the structural components of lignocellulosic materials. However, Kerr et al. (1983 unpublished data) found that treatment of peanut hulls with acid or base at 121° C. increased the relative lignin content (except for 0.5N $HNO_3$), while substantially decreasing protein content. Changes in the relative percentage of cellulose ranged from a decrease of 27% to an increase of 22%, depending on the treatment. Thus, treatments at elevated temperatures have generally not been effective in disrupting the structural integrity of peanut hulls.

The present invention discloses a process for improving both the digestibility and nutritional value of peanut hulls using a combination of chemical treatment and lignin degradation with the microorganism KB-1.

Peanut hulls are not only low in digestibility (15–25%), but also low in both fat (less than 1%) and protein (6–8%). To increase the amount of protein, (Beuchat, L. R., Agr. Exp. Sta. (Ga.) Res. Report 240, 7 pp., 1977) grew *Trichoderma viride* (reesei) on peanut hulls supplemented with ammonium sulfate and increased the protein content by as much as 63% (from 7.7% to 12.1%). In addition to investigating digestibility of hulls after chemical and biological treatment, we assessed changes in protein content and digestibility upon the addition of the yeast, *Saccharomyces cerevisiae*.

It is an object of the present invention to provide a microorganism having the ability to utilize peanut hull lignin as a sole source of carbon and by so doing to provide a process for increasing the digestability and nutritional value of peanut hulls for use as animal feed.

These and other objects, aspects, and advantages of this invention will become apparent from a consideration of the accompanying specification and claims.

DESCRIPTION OF THE PREFERRED EMBODIMENTS

Microorganisms suitable for practicing the processes and procedures of the present invention described herein are exemplified by cultures now on Deposit with the American Type Culture Collection, 12301 Parklawn Drive, Rockville, Md. 20852, USA. These cultures were deposited on the tenth day of November, 1983, and are identified by ATCC No. 39507. Prior to the above described deposit, strain KB-1 was not available outside the research facilities of the joint inventors.

Forty-two different types of microorganisms were isolated from decaying peanut hulls utilizing water extracted hulls and four different lignin preparations isolated from peanut hulls as shown in Table 1, below. Of this number, eleven were isolated from media containing water extracted hulls (P-1, P-2, P-4 through P-6, and P-8 through P-13), ten from media containing Klason lignin (K-1 and K-3 through K-11), fourteen from media containing hydrochloric acid lignin (H-1 through H-8, H-10, N-11, and H-14 through H-17), four from media containing dioxane lignin (D-1 through D-4), and four from media containing milled wood lignin (M-1 through H-4). A majority of the isolates (thirty) grew on water extracted hulls and over half (twenty-three) grew on the milled wood lignin preparation. Only eight of the isolates grew on dioxane lignin, but all of the isolates from the dioxane lignin culture grew on water extracted peanut hulls and three out of four grew on milled wood lignin. It is also interesting to note that very few of the isolates grew on Klason lignin, with the exception of the microorganism originally isolated from the Klason lignin cultures.

Only one microorganism isolate was capable of utilizing all five materials as a sole carbon source, although sixteen isolates grew on three of the five preparations. The preferred microorganism capable of growing on all five preparations was K-7. This isolate was redesignated KB-1 to indicate that it was the only isolate capable of utilizing all five peanut hull preparations as a carbon source. When inoculated onto agar plates containing basal salts but without a carbon source, KB-1 did not grow.

When grown in the Klason-lignin media for 24 hours at 26° C., KB-1 appeared as a gram positive, short, stubby rod that possessed a spore-like vacuole situated in the middle of the cell. This vacuole did not retain the gram stain, and thus appeared to be hollow. When KB-1 was subjected to a spore stain, it failed to show any sign of a spore. When grown in nutrient broth at 26° C. in a shaking incubator for 24 hours and gram stained, KB-1 appeared as a small, gram negative cocci with a few (less than 1%) larger cocci that were gram positive.

Biochemical testing of KB-1 indicates that it can use a number of carbohydrates as carbon sources including glucose, maltose, xylose, mannose, and sucrose, but it is not capable of using lactose or arabinose as shown in Table 2, below. The inability to utilize arabinose as a carbon source was unexpected because arabinose is one of the primary carbohydrates found in peanut hulls. The microorganism KB-1 is catalase positive, $NO_2$ positive, and utilizes citrate, which are three of the main biochemical tests used in the identification of Arthrobacter. Although KB-1 is gram positive during a portion of its life cycle, it is not sensitive to penicillin or ampicillin, but is extremely sensitive to chloramphenicol, sulfathiozol, tetracycline, and kanamycin.

Degradation of radiolabeled substrates by KB-1

After ten days of incubation, KB-1 mineralized (degraded material to $CO_2$) a significant fraction of the lignin (3%) and polysaccharide (6.5%) portion of Spartina $^{14}C$-lignocellulose. KB-1 degraded the lignin and cellulosic portions of the lignocellulose simultaneously. Rates of degradation were most rapid during the first six days of incubation. The $^{14}C$-Kraft lignin was mineralized at 30% of the mineralization rate of $^{14}C$-(lignin)-lignocellulose from Spartina. The lignin portion of Spartina lignocellulose has been reported to be mineralized approximately 4 to 6 times faster than Kraft lignin by natural microbial populations found in salt marsh sediments (Hodson, R. E., R. Benner, and A. E. Maccubbin, Biodeterioration 5, 185–195, 1983; Maccubbin, A. E., R. Benner, and R. E. Hodson, Biodeterioration 5, 246–256, 1983). In the presence of added cellulose, KB-1 mineralized $^{14}C$-Kraft lignin at 67% of the rate in the absence of added cellulose.

TABLE 1

Growth of Microorganism Isolates on Minimal Media with Various Carbon Sources[a]

| Microorganism | Peanut Hull[b] | Klason Lignin | HCl-Lignin | Dioxane-Lignin | Milled Wood Lignin |
|---|---|---|---|---|---|
| P-1 | + | − | + | − | + |
| P-2 | + | − | − | − | + |
| P-4 | + | + | − | − | − |
| P-5 | + | − | − | − | − |
| P-6 | + | − | − | − | + |
| P-8 | + | − | + | + | − |
| P-9 | + | − | − | − | + |
| P-10 | + | − | − | − | + |
| P-11 | + | − | − | − | − |
| P-12 | + | − | − | − | − |
| P-13 | + | − | − | − | + |
| K-1 | + | + | − | − | + |
| K-3 | + | + | − | − | + |
| K-4 | − | − | − | − | + |
| K-5 | + | + | − | − | − |
| K-6 | − | + | − | − | − |
| K-7 (KB-1) | + | + | + | + | + |
| K-8 | − | + | − | − | − |
| K-9 | + | − | − | − | − |
| K-10 | + | + | + | − | − |
| K-11 | − | + | − | − | + |
| H-1 | + | − | + | − | + |
| H-2 | − | + | + | + | − |
| H-3 | + | − | + | − | + |
| H-4 | + | − | + | − | + |
| H-5 | − | + | + | + | − |
| H-6 | − | + | + | + | − |
| H-7 | − | − | + | − | + |
| H-8 | − | − | + | − | − |
| H-10 | + | − | − | − | − |
| H-11 | + | − | + | − | + |
| H-14 | − | − | + | − | − |
| H-15 | + | − | + | − | + |
| H-16 | − | − | + | − | − |
| H-17 | − | − | + | − | − |
| D-1 | + | − | − | + | + |
| D-2 | + | − | − | + | + |
| D-3 | + | − | + | − | − |
| D-4 | + | − | − | + | + |
| M-1 | + | − | − | − | + |
| M-3 | + | − | − | − | + |
| M-4 | + | − | − | − | + |

[a] Several (7) isolates did not grow upon transfer to fresh media, and they were omitted from the table.
[b] Water extracted hulls

TABLE 2

Dye Sensitivity, Antibiotic Susceptibility, Biochemical, and Fermentation Reactions of KB-1

| | | | |
|---|---|---|---|
| Arginine dihydrolase | − | Ampicillin | − |
| Lysine decarboxylase | − | Tetracycline | ++ |
| Ornithine decarboxylase | − | Chloramphenicol | ++++ |
| Citrate | + | Sulfathiozol | +++ |
| $H_2S$ | − | Kanamycin | ++ |
| Urease | − | Novobiocin | + |
| Tryptophane deaminase | − | Polymyxin B | + |
| Indole | − | Neomycin | + |
| VP | + | Vancomycin | − |
| Gelatin | − | Lactose | − |
| Oxidase | − | Mannitol | − |
| Catalase | + | Inositol | − |
| Methyl Red | − | Sorbitol | − |
| Maltose | +Gas | Rahmnose | − |
| Glucose | + | Sucrose | + |
| Xylose | +Gas | Melobiose | − |
| Mannose | +Gas | Amygdalin | − |
| Sucrose | + | Arabinose | − |
| Dyes - Sensitive | | Motility | − |
| Malachite green | + | Fat Hydrolysis | − |
| Crystal violet | + | DNAse Activity | − |
| Methyl green | + | Starch Hydrolysis | − |
| Antibiotic Susceptibility | | $NO_2$ | − |
| Streptomycin | ++ | $N_2$ | + |
| Penicillin | − | Blood Agar | gamma |
| Rifampicin | − | Gram Stain | +/− |
| Bacitracin | − | Morphology | Variable rods/cocci |
| Erythromycin | + | | |
| TSI | | | |
| Slant | Acid | | |

TABLE 2-continued

Dye Sensitivity, Antibiotic Susceptibility,
Biochemical, and Fermentation Reactions of KB-1

| Base | Acid |
|---|---|
| $H_2S$ | — |
| Gas | + + |

Growth of the Bacterium KB-1

Of the temperatures tested, maximal growth of the bacterium KB-1 occurred at 26° C. Data presented in Table 3, below, demonstrates the ability of the bacterium to grow rapidly on the peanut hulls before and after the various chemical treatments. Growth on peanut hulls was comparable to growth in nutrient broth. On the untreated hulls and hulls treated with 2% NaOH or the acetic acid:nitric acid mixture, optimum growth occurred at pH9. Hulls treated with HCl, $HNO_3$, 1% NaOH, or calcium hypochlorite had optimal growth at pH7; whereas, hulls treated with $H_2SO_4$, $NH_4OH$, or 4% NaOH demonstrated optimal growth at pH5.

Chemical Treatments

The chemical composition of peanut hulls after various chemical treatments at room temperature is given in Table 4. A marked increase in the relative percentage of protein in all cases was observed. The greatest increases were in peanut hulls treated with 4% NaOH, calcium hypochlorite, or the acetic acid-nitric acid mixture, all of which more than doubled the percentage of protein. A minor increase in the relative percentage of protein occurred when the hulls were treated with 1% NaOH or sulfuric acid. While chemical treatments increased the relative percentage of protein, such treatments decreased the relative percentage of lignin in each of the samples. The nitric acid treatment decreased the relative amount of measurable lignin in the hull by over 55%, while 2% NaOH, 4% NaOH, or calcium hypochlorite decreased it by approximately 36%. The other treatments decreased the lignin content by less than 25%.

The cellulose content of the treated peanut hulls varied from a relative loss of 46% for peanut hulls treated with calcium hypochlorite to a relative increase of 58% for hulls treated with nitric acid. In addition to calcium hypochlorite, sulfuric acid, and 4% sodium hydroxide treatments reduced the relative percentage of cellulose in the hulls, while the other five treatments increased the relative percentage of cellulose by an average of 28%.

The amount of carbohydrate in the hulls decreased after all the treatments, especially sulfuric acid, hydrochloric acid, and ammonium hydroxide, which decreased the carbohydrate content to less than 1 mg per gram of peanut hull. Of the remaining six (6) treatments, 4% NaOH caused the smallest loss of carbohydrate, 20%, while the other five treatments effected less than a 50% loss of carbohydrates.

Chemical analyses of the various treated and untreated hulls after growth of the bacterium KB-1 for 24 hours are presented in Table 5. In comparison with the uninoculated peanut hulls as shown in Table 2, below, seven of the ten samples showed an increase in protein content. The most significant increase of protein content was in the untreated hulls which increased by over 100%. Hulls treated with sulfuric acid, 1% NaOH, 2% NaOH also significantly increased the percentage of protein by 82%, 60%, and 59%, respectively. Hulls treated with the acetic acid-nitric acid mixture decreased in the percentage of protein (52%), followed by hulls treated with nitric acid (16%) and 4% NaOH (15%).

The percentage of lignin decreased in six of the ten samples inoculated with the microorganism KB-1 as shown in Table 5, below, in comparison with uninoculated hulls as shown in Table 4, below. Untreated hulls decreased by 38% in the percentage of lignin, while hulls treated with sulfuric acid, nitric acid, ammonium hydroxide, acetic acid-nitric acid mixture, or 1% NaOH decreased by less than 25% in the percentage of lignin. Hydrochloric acid, 2% NaOH, 4% NaOH, or calcium hypochlorite treated hulls increased in the percentage of lignin by 9%, 12%, 33%, and 6%, respectively.

In comparison with uninoculated peanut hulls as shown in Table 4, below, after growth of the microorganism KB-1 the percentage of cellulose remained approximately the same for untreated hulls and hulls treated with nitric acid, but decreased significantly for hulls treated with 1% NaOH, 2% NaOH, calcium hypochlorite, acetic acid-nitric acid mixture, or ammonium hydroxide. Peanut hulls treated with hydrochloric acid, sulfuric acid, or 4% NaOH increased in the percentage of cellulose. The amount of carbohydrate decreased in the majority of samples except for the hulls treated with nitric acid, which demonstrated an increase of 18%. Two other samples retained a portion of their original carbohydrate, the peanut hulls treated with 4% NaOH and hulls treated with the acetic acid-nitric acid mixture.

In an attempt to increase the protein content of the hulls after chemical treatment and growth of the microorganism KB-1, the yeast, *Saccharomyces cerevisiae,* was added to each treatment and incubated for an additional 24 hours. Chemical analyses of treatments after growth of *S. cerevisiae* are presented in Table 6, below. In most cases, the percentage of protein decreased after 24 hour incubation of *S. cerevisine* in comparison to the percentage of protein after growth of the microorganism KB-1. Hulls treated with $HNO_3$ or the acetic acid-nitric acid mixture did increase in the percentage of protein (30% and 12%, respectively) after growth of *S. cerevisiae.*

Digestibility

Peanut hulls are very resistant to biodegradation, and they are only minimally digestible in rumen liquor (Kerr et al., unpublished data; Barton, F. E., H. E. Amos, W. W. Albrecht and D. Burdick, J. Anim. Sci. 38:860–864, 1974). Certain chemical components of plant fiber, such as lignin, impede microbial degradation and thus, reduce digestibility of the material. Peanut hulls contain more lignin (31–33%) than most hardwoods and softwoods, and the low digestibility of hulls could result from the high lignin concentration. However, after several chemical delignification procedures at elevated temperatures, the digestibility of hulls has been found to decrease (Kerr et al., unpublished data; Barton, F. E., H. E. Amos, W. W. Albrecht and D. Burdick, J. Anim. Sci. 38:860–864, 1974). Likewise, the relatively mild chemical treatments used in this study, which were effective in removing lignin, did not significantly increase the digestibility of the hulls (except 4% NaOH, Table 2). Instead these treatments decreased digestibility by as much as 93%.

Most of the chemical treatments also effectively increased the relative percentages of protein and cellulose in the hulls as shown in Table 4, below. The protein and cellulose portions of plant mateial are generally very digestible, and any relative increase in these components should increase digestibility. However, chemical treatments which increased the relative percentages of protein and cellulose actually decreased the digestibility of peanut hulls as shown in Table 4, below. The chemical treatments used in this study appear to remove the more labile, digestible components of peanut hulls without disrupting the structural integrity of the lignocellulosic fiber.

Pretreatment of hulls with $HNO_3$ decreased the lignin concentration by 55%, and increased the cellulose concentration by 58%. The ratio of lignin to cellulose was 2:7, but digestibility was still lower than digestibility of untreated hulls which had a lignin to cellulose ratio of approximately 1:1. The chemical and physical complexing with the polysaccharide faction and between the remaining lignin and polysaccharide fractions appeared to be intact. After growth of the bacterium Kb-1 on $HNO_3$ pretreated hulls, the ratio of lignin to cellulose dropped even lower to approximately 2:9 (Table 5). There was a dramatic increase in digestibility from 14.9% to 63.2%, an increase of over 400%. This compares favorably to commercially available hay. All other treatments effected much higher lignin to cellulose ratios, and they all decreased in digestibility after growth of the microorganism KB-1 as shown in Table 5, below. Treatment with $HNO_3$ appears to remove the "protective" lignin and expose the remaining bonds between the lignin and cellulose to bacterial exoenzymes.

More recent tests of the present invention have shown that the autoclaving steps are not necessary. By eliminating such steps digestibility may be increased above the 60% level. In addition several strains of microorganism (University of Georgia, Dept. of Microbiology, Stock Cultures of *Bacillus subtilis, Klebsiella pneumoniae,* and *Escherichia coli*) and a natural soil inoculum failed to increase the protein digestibility of $HNO_3$ treated peanut hulls. The growth of the yeast, *S. cerevisiae*, on $HNO_3$ treated peanut hulls did not significantly increase protein digestibility as shown in Table 6, below; therefore, such growth step with yeast is not necessary. Therefore a prolonged incubation of the microorganism KB-1 can be utilized to increase the amount of protein and increase digestibility.

TABLE 3

Growth of Arthrobacter KB-1 at 26° C. (CFUs)

| Treatment | pH 5 | pH 7 | pH 9 |
|---|---|---|---|
| Nutrient Broth | $4.67 \times 10^9$ | $2.52 \times 10^9$ | $5.15 \times 10^9$ |
| Untreated hulls | $1.56 \times 10^9$ | $1.55 \times 10^9$ | $2.61 \times 10^9$ |
| HCl | $1.81 \times 10^9$ | $1.01 \times 19^{10}$ | $2.31 \times 10^9$ |
| $H_2SO_4$ | $1.07 \times 10^{10}$ | $2.3 \times 10^9$ | $1.7 \times 10^9$ |
| $HNO_3$ | $1.75 \times 19^9$ | $1.15 \times 19^{10}$ | $3.2 \times 10^8$ |
| $NH_4OH$ | $1.18 \times 10^{10}$ | $3.0 \times 10^9$ | $1.2 \times 10^9$ |
| 1% NaOH | $4.5 \times 10^8$ | $1.0 \times 10^9$ | $6.6 \times 10^8$ |
| 2% NaOH | $1.0 \times 10^9$ | $8.3 \times 10^8$ | $1.87 \times 10^9$ |
| 4% NaOH | $1.14 \times 10^9$ | $7.7 \times 10^8$ | $2.6 \times 10^8$ |
| Ca. Hypochlorite | $0.1 \times 10^8$ | $1.8 \times 10^9$ | $1.6 \times 10^9$ |
| Acetic Acid-$HNO_3$ | $5.7 \times 10^8$ | $9.3 \times 10^8$ | $1.2 \times 10^{10}$ |

TABLE 4

Chemical Composition and Digestibility of Chemically Treated Peanut Hulls

| Treatment | Protein (%) | Lignin (%) | Cellulose (%) | Carbohydrate (mg/gram) | Digestibility (%) |
|---|---|---|---|---|---|
| Untreated hulls | 6.5 | 31.1 | 32.0 | 17.5 | 17.52 |
| HCl | 10.2 | 23.4 | 40.0 | 1.0 | 1.20 |
| $H_2SO_4$ | 7.4 | 28.8 | 28.0 | 1.0 | 1.24 |
| $HNO_3$ | 12.5 | 13.9 | 50.5 | 10.0 | 14.91 |
| 1% NaOH | 7.5 | 24.2 | 42.0 | 10.4 | 14.07 |
| 2% NaOH | 9.1 | 19.9 | 40.0 | 12.0 | 16.85 |
| 4% NaOH | 14.2 | 19.9 | 30.5 | 14.0 | 18.91 |
| Ca. Hypochlorite | 13.1 | 20.1 | 17.0 | 9.2 | 16.72 |
| Acetic Acid-$HNO_3$ | 14.2 | 27.6 | 40.0 | 11.1 | 7.51 |
| $NH_4OH$ | 10.5 | 25.9 | 43.0 | 1.0 | 4.14 |

TABLE 5

Chemical Composition and Digestibility of Chemically Treated Peanut Hulls After Growth of Arthrobacter KB-1

| Treatment | Protein (%) | Lignin (%) | Cellulose (%) | Carbohydrate (mg/gram) | Digestibility (%) |
|---|---|---|---|---|---|
| Untreated | 14.0 | 19.3 | 32.0 | 1.0 | 8.56 |
| HCl | 14.0 | 25.5 | 48.5 | 1.0 | 1.74 |
| $H_2SO_4$ | 13.5 | 21.9 | 35.5 | 1.0 | 0.47 |
| $HNO_3$ | 10.5 | 10.7 | 50.0 | 11.8 | 63.22 |
| 1% NaOH | 12.0 | 23.6 | 26.0 | 1.0 | 7.37 |
| 2% NaOH | 14.5 | 22.3 | 22.8 | 1.0 | 10.47 |
| 4% NaOH | 12.0 | 26.4 | 40.2 | 5.2 | 9.55 |
| Ca. Hypo- | 17.5 | 21.4 | 8.0 | 1.0 | 11.52 |
| Acetic Acid-$HNO_3$ | 6.8 | 24.8 | 16.0 | 7.0 | 7.45 |
| $NH_4OH$ | 11.4 | 19.9 | 36.5 | 1.0 | 1.59 |

TABLE 6

Protein Content and Digestibility of Chemically Treated Peanut Hulls After Growth of Arthrobacter KB-1 and *S. cerevisiae*

| Treatment | Protein (%) | Digestibility (%) |
|---|---|---|
| Untreated hulls | 12.7 | 9.07 |
| HCl | 9.0 | 2.09 |
| $H_2SO_4$ | 8.2 | 0.86 |
| $HNO_3$ | 13.6 | 63.32 |
| 1% NaOH | 5.6 | 9.47 |
| 2% NaOH | 7.8 | 12.86 |
| 4% NaOH | 9.8 | 11.14 |
| Ca. Hypochlorite | 17.5 | 13.24 |
| Acetic Acid-$HNO_3$ | 7.6 | 9.07 |
| $NH_4OH$ | 8.5 | 5.84 |

Materials and Methods

Lignin Preparations

Peanut hulls were supplied by the Columbian Peanut Company of Ozark, Ala., and Stevens Industries, Dawson, Ga. The peanut, *Arachis hypogeae*, was of the Florunner variety and was hammer milled to ¼" in size. Hammer milling to less than ¼" in size is also acceptable. Before use as a growth substrate, peanut hulls were extracted with boiling water for 1 hour (4 changes of water during extraction), and dried for 24 hours at 70° C. Lignin was isolated from peanut hulls by four different procedures:

1. Dioxane Lignin—¼" hammer milled peanut hulls were extracted in a Soxhlet extractor for 50 hours with a boiling ethanol-benzene (1:1) and dried in a vacuum dissicator. Extractive-free hulls were then extracted for 12 hours with boiling dioxane-water (9:1) containing the equivalent of 0.2N HCl. The extract was concentrated under vacuum and the lignin was precipitated in deionized distilled water. The precipitated lignin was washed with water three times, dried, and washed with petroleum ether (Browning, B. L., 1967. Methods of Wood Chemistry, Vol. II. Interscience Publishers, Inc.).

2. Milled Wood Lignin—¼" hammer milled peanut hulls were extracted with boiling ethanol-benzene (1:2) for 48 hours, and then with 95% ethanol for 24 hours. Extractive-free hulls were ball milled for 9 days. Milled hulls were extracted with boiling dioxane-water (9:1) for 12 hours. The solvent was concentrated under vacuum, and the lignin was precipitated in water. The precipitated lignin was thoroughly washed with petroleum ether (Browning, B. L., 1967. Methods of Wood Chemistry, Vol. II. Interscience Publishers, Inc.).

3. Klason Lignin—Extractive-free hulls (as described above) were treated with 72% sulfuric acid at 15° C. for 2 hours. The mixture was diluted with water to a 3% acid concentration and refluxed for 4 hours. The residue was washed thoroughly with water (Browning, B. L., 1967. Methods of Wood Chemistry, Vol. II. Interscience Publishers, Inc.).

4. Hydrochloric Acid Lignin—¼" hammer milled hulls were treated with hydrochloric acid (sp gr 1.19 at 5° C.) at 5° C. for 2 hours in a shaking incubator. The temperature was allowed to rise to room temperature. Ice was added to the mixture which was allowed to stand for 18 hours. The precipitate was washed with boiling water, filtered, and dried (Browning, B. L., 1967. Methods of Wood Chemistry, Vol. II. Interscience Publishers, Inc.).

Lignin and peanut hulls (extracted with boiling water) were used at a concentration of 0.5 g per liter in both solid and liquid media. Hulls used in liquid media were ball milled to pass through a 0.1 mm sieve. Lignins and hulls used in solidified media were dissolved in 0.25N NaOH (0.5 g hulls:10 ml NaOH), filtered, and added to sterile basal media (7 g $K_2HPO_4$, 3 g $KH_2PO_4$, 1 g $(NH_4)_2SO_4$, 0.1 g $MgSO_4.7H_2O$ per liter of tap water). An equivalent amount of sterile 0.25N HCl was added to the sterile media.

Preparation of $^{14}C$-lignocelluloses and $^{14}C$-Kraft lignin

The smooth cordgrass, Spartina alterniflora, was specifically labelled in the lignin or cellulosic components by feeding cuttings L-[U-$^{14}C$] phenylalanine or D-[U-$^{14}C$] glucose through their cut stems (Crawford, D. L., R. L. Crawford and A. L. Pometto, III, Appl. Environ. Microbiol. 33:1247–1251, 1977; Maccubbin, A. E. and R. E. Hodson, Appl. Environ. Microbiol. 40:735–740, 1980). The labelled material was dried and ground to pass a 40-mesh screen. The plant material was then serially extracted in boiling ethanol, ethanol-benzene (1:2), and water (Maccubbin, A. E. and R. E. Hodson, Appl. Environ. Microbiol. 40:735–740, 1980). Extractive-free lignocellulose was collected on a glass fiber filter, washed with ethanol, and dried at 55° C. The $^{14}C$-labelled lignocelluloses were characterized for the distribution of $^{14}C$ between the lignin and polysaccharide components by a Klason hydrolysis as previously described (Maccubbin, A. E. and R. E. Hodson, Appl. Environ. Microbiol. 40:735–740, 1980). Samples of $^{14}C$-lignocellulose were also digested in the protease, pepsin, to determine the percentage of radiolabel possibly associated with protein (Maccubbin, A. E. and R. E. Hodson, Appl. Environ. Microbiol. 40:735–740, 1980). The specific activities of $^{14}C$-lignocelluloses were determined by combusting 10 mg samples in a R. J. Harvey Biological Oxidizer and trapping the released $^{14}CO_2$ is a liquid scintillation medium (Maccubbin, A. E. and R. E. Hodson, Appl. Environ. Microbiol. 40:735–740, 1980).

The lignin labelled Spartina lignocellulose had a specific activity of 23,238 dpm per mg, 70.9% of the label was recovered in the Klason lignin fraction, and 19.0% of the label was solubilized during pepsin digestion. The polysaccharide labelled Spartina lignocellulose had a specific activity of 6,889 dmp. per mg., 61.9% of the label was recovered in the acid-soluble fraction, and 21.9% of the label was solubilized during pepsin digestion.

Wood from the slash pine, Pinus elliottii, was labelled in the lignin component using the methods described above for labelling Spartina. The lignin labelled pine lignocellulose had a specific activity of 2,825 dpm per mg, 90% of the label was recovered in the Klason Lignin fraction, and 2.8% of the label was solubilized during pepsin digestion. After extracting the wood to remove unincorporated label, the $^{14}C$-(lignin)-lignocellulose was "pulped" using a laborator-scale Kraft pulping system (Chang, H. and K. V. Sarkanen, TAPPI 56:132–134, 1973; Crawford, D. L., S. Floyd, A. L. Pometto, III, and R. L. Crawford, Can. J. Microbiol. 23:434–440, 1977; Maccubbin, A. E., R. Benner and R. E. Hodson, Biodeterioration 5, p. 246–256, 1983). The $^{14}C$-lignocellulose was heated to 160° C. for 4 hours in Kraft pulping liquor (1:25M NaOH and 0.25M $Na_2S$). After cooling, the mixture was filtered and $^{14}C$-Kraft lignin was precipitated from the pulping liquor by acidification to pH 2. The precipitated lignin was centrifuged and washed with deionized water (3 times). The specific activity of the $^{14}C$-Kraft lignin was 2,904 dpm per mg.

Isolation of lignin-degrading bacteria

Decaying peanut hulls were obtained from the bottom of a peanut hull pile situated on a farm in Salem, Ala. The hulls had been weathered in the open for approximately 5 years and showed signs of physical degradation. Five (5) 250 ml flasks were prepared, each containing 100 mls of basal salts solution and 50 mg of hulls or one of the four (4) lignins. Approximately 10 ml of decaying hulls were placed in 100 mls of sterile saline and shaken for 5 minutes. One (1) ml aliquots were used to inoculate the five (5) 250 ml flasks. The flasks were incubated at 26° C. for 24 hours in a shaking incubator, then 0.1 ml aliquots were used to inoculate agar plates containing basal salts and hulls or one of the lignin preparations. Plates were incubated for 24 hours at 26° C. Each colony was picked and streaked on five (5) agar plates containing basal salts media and one of the five (5) substrates (hulls or lignins) used as carbon sources. The microorganism strain, KB-1, that grew on all five (5) carbon sources was tested for its sensitivity to various dyes, antibiotics, and biochemical reactions as described herein. See Table 2.

Degradation of $^{14}C$-lignocelluloses and $^{14}C$-Kraft lignin

The bacterial isolate capable of growing on all four lignin preparations as well as water extracted hulls was grown overnight (shaking, 26° C.) in basal salts media containing Spartina lignocellulose. After permitting the larger lignocellulose particles to settle, 20 ml portions were added to 125 ml milk dilution bottles containing 10 mg of one of the following: $^{14}C$-(lignin)-lignocellulose from Spartina, $^{14}C$-(cellulose)-lignocellulose from Spartina, or $^{14}$C-Kraft lignin degradation, 20 mg of alpha cellulose were added to one set of bottles. Bottes were incubated in duplicate, in the dark, at 30° C. with shaking (125 rpm). Controls were killed with 5% Formalin. Mineralization of the radiolabelled substrates was monitored every 48 hours by trapping the evolved $^{14}CO_2$ in a series of two scintillation vials containing liquid scintillation counting medium (Maccubbin, A. E. and R. E. Hodson, Appl. Environ. Microbiol. 40:735–740, 1980). Water-soluble $^{14}$C present in the incubations containing $^{14}$C-lignocellulose from Spartina was quantified by filtering the contents of the bottle through 1 m Nuclepore filters, acidifying the filtrate to remove $^{14}CO_2$, and assaying 1 ml portions for radioactivity.

Chemicals and Radioisotopes

All chemical utilized in the treatment, extraction, and analysis of peanut hulls were reagent grade and were obtained from either Fisher Chemical Co., Norcross, Ga., or Sigma Chemical Co., St. Louis, Mo. Radioisotopes, D-[U-$^{14}$C]-glucose and L-[U-$^{14}$C]-phenylalanine were obtained from New England Nuclear Corp., Boston, Mass.

All Preparations Except Lignin Preparations Described Above

Peanut hulls utilized in this study were supplied by the Columbian Peanut Company, Ozark, Ala., and the Damascus Peanut Company, Damascus, Ga. The peanut (*Arachis hypogeae*) from which the hull was obtained was the Florunner variety. Hulls were hammer-milled to ¼" in size. All chemicals used were reagent grade and were obtained from Sigma Chemical Company, St. Louis, Mo., or Fisher Scientific Company, Norcross, Ga.

Growth of Inoculum

The microorganism KB-1 was grown for 16 hours in 100 mls of a basal salt solution (7.0 g $K_2HPO_4$, 3.0 g $KH_2PO_4$, 1.0 g $NHSO_4$, 0.1 g $MgSO_4.7H_2O$) containing 5 g of hammer milled peanut hulls that had been extracted twice with hot water and then oven dried at 70° for 24 hours. The culture was grown in a shaking incubator at 25° C. The culture was removed from the incubator and allowed to stand for 1 hour, permitting the peanut hulls to settle to the bottom. The liquid was pipeted off, placed in sterile centrifuge tubes, centrifuged in a Sorvall table top centrifuge at 1725 RPM for 15 minutes, washed one time with sterile saline, then resuspended in 100 mls of sterile saline.

Chemical Treatments of Peanut Hulls

One (1) liter portions of hammer milled peanut hulls (approximately 255 g) were soaked for one (1) hour at room temperature (25° C.) in two (2) liters of one of the following solutions: 0.5N hydrochloric acid, 0.5N nitric acid, 0.5N sulfuric acid, 0.5N ammonium hydroxide, 1% sodium hydroxide, 2% sodium hydroxide, 4% sodium hydroxide, 1M calcium hypochlorite, or 80% acetic acid:Conc. nitric acid (1:10). After treatment, hulls were thoroughly rinsed three (3) times in tap water.

Optimum pH and Temperature for Growth of Arthrobacter KB-1

Nine (9) flasks of each treatment were prepared by adding 50 mls of wet hulls to 100 mls of basal salts media (as above). Of the nine flasks, triplicates of each treatment were adjusted to pH 5, 7, or 9 with 1N NaOH and 1N HCl. The flasks were then autoclaved for 15 minutes at 15 psi, cooled, and inoculated with 0.5 ml of KB-1 inoculum. One (1) flask of each treatment adjusted to pH 5, 7, or 9 was incubated for 24 hours at 26°, 30°, or 45° C. in a shaking incubator. After 24 hours, dilutions of the cultures were made into sterile saline and spread plates on nutrient agar were prepared. Plates were incubated at room temperature for 20 hours and colonies counted.

Changes in Chemical Composition and Digestibility

Four (4) samples of each treatment were prepared by placing 100 mls of wet hulls into a 500 ml erlenmeyer flask and adding 100 mls of basal salts solution. The pH was adjusted for optimal growth and flasks were inoculated with 0.5 ml of the microorganism KB-1, prepared as described above. All flasks were incubated at 26° C. for 24 hours in a shaking incubator. After 24 hours, two flasks of each treatment were autoclaved for 15 minutes at 15 psi, cooled, filtered through cheese cloth and dried at 70° C. for 24 hours. The other two flasks from each treatment were inoculated with 0.5 mls of *S. cereviseae* which had been grown overnight in Sabouraud Dextrose Broth on a shaking incubator at 26° C., centrifuged at 1725 RPM for 15 minutes in a Sorvall table top centrifuge, washed one time in sterile saline, and then resuspended in 100 mls of sterile saline. Flasks were incubated for an additional 24 hours at 26° C. in a shaking incubator, autoclaved for 15 minutes at 15 psi, cooled, filtered through cheese cloth and dried at 70° C. for 24 hours.

Samples of the (1) chemically treated hulls, (2) chemically treated hulls used as a substrate for the microorganism KB-1, and (3) chemically treated hulls used as a substrate for the microorganism KB-1 and *S. cereviseae* were analyzed for protein, cellulose, lignin, total carbohydrate, and digestibility. Samples were analyzed for protein by the Kjeldhal method (AOAC, Official McMeds of Analysis, 12th Ed., 1979, p. 927–928, Association of Official Analytical Chemists, Washington, D.C.), for cellulose by the Updergraff method (Updegraff, D. M., Anal. Biol. 32:420–424, 1969), for lignin by a modified Klason method (Effland, M. J., TAPPI 60:143–144, 1977), and for in vitro dry matter digestibility (IVDMD) by the Tilley and Terry method (Tilley, J. M. A. and R. A. Terry, J. Brit. Grass Soc. 18:104–111, 1963), wherein all such methods are known in the art.

Solid Innoculum

A solid innoculum is prepared for the microorganism KB-1 comprising the microorganism KB-1 and a solid carrier containing standard nutrient growth medium.

Liquid Innoculum

A liquid innoculum is prepared for the microorganism KB-1 comprising the microorganism KB-1 and an aqueous carrier containing a standard nutrient growth medium.

Organic Material

The microorganism KB-1 is capable of degrading lignin from any organic material having a high lignocellulose content wherein the organic material is from a natural source such as a plant. A high lignocellulose content is a lignin content of 20% or greater of the organic material and a cellulose content of 20% or greater of the organic material. The microorganism KB-1 is capable of degrading lignin from peanut hulls, softwoods, hardwoods, pulp wood, slash pine, cordgrass, barley hulls, cotton seed hulls, wheat straw, and the like. Such organic material having a high lignocellulose content, peanut hulls, wheat straw, barley hulls, cotton seed hulls and the like are converted into animal feed wherein digestibility is increased by degrading the lignin therein utilizing the microorganism KB-1. Chemical pretreatment improves the production of such animal feed wherein nitric acid is the preferred chemical for chemical pretreatment. The microorganism KB-1 degrades lignin with maximum efficiency and growth of the microorganism at 26° C.

The foregoing illustrates specific embodiments within the scope of this invention and is not to be construed as limiting said scope. While the invention has been described herein with regard to a certain specific embodiment, it is not so limited. It is to be understood that variations and modifications thereof may be made by those skilled in the art without departing from the scope of the invention.

We claim:

1. A biologically pure culture of a microorganism having all the identifying characteristics of Arthrobacter KB-1 or a mutant thereof.

2. A solid inoculum suitable for use in a process for degrading lignin, comprising:
   (a) a microorganism in biologically pure form having all the identifying characteristics of Arthrobacter KB-1 or a mutant thereof, and
   (b) a solid carrier.

3. A liquid inoculum suitable for use in a process for degrading lignin, comprising:
   (a) a microorganism in biologically pure form having all the identifying characteristics of Arthrobacter KB-1 or a mutant thereof, and
   (b) an aqueous carrier.

4. A process for degrading lignin, which comprises: treating an organic material having a high lignocellulose content under conditions sufficient to degrade lignin with a microorganism having all the identifying characteristics of Arthobacter KB-1 or a mutant thereof.

5. The process of claim 4 wherein said organic material has a lignin content of 20% or greater of said organic material and a cellulose content of 20% or greater of said organic material.

6. The process of claim 4 wherein said organic material is a plant or plant part comprising lignin.

7. The process of claim 6, wherein said lignin is peanut hull lignin.

8. The process of claim 6 wherein said lignin is wood lignin selected from the group consisting of hardwood lignin and softwood lignin.

9. The process of claim 6 wherein said lignin is pulp wood lignin.

10. The process of claim 6 wherein said lignin is slash pine lignin.

11. The process of claim 6 wherein said lignin is cordgrass lignin.

12. The process of claim 6 wherein said lignin is wheat straw lignin.

13. The process of claim 6 wherein said lignin is barley hull lignin.

14. The process of claim 6 wherein said lignin cotton seed hull lignin.

15. A process for feeding animals, which comprises:
   increasing the digestability of an organic material having a high lignocellulose content by treating the organic material with a microorganism having all the identifying characteristics of Arthobacter KB-1 or a mutant thereof, thereby reducing the lignin content of said material; and
   feeding said material having a reduced lignin content to an animal.

16. The process of claim 15 wherein said material having a reduced lignin content is utilized as a cattle feed.

17. The process of claim 15, wherein said organic material is chemically pretreated with nitric acid prior to treatment with said microorganism.

18. The process of claim 15 wherein said organic material is a peanut hull, wheat straw, barley hull, or cotton seed hull.

19. The process of claim 18 wherein said organic material is chemically pretreated with nitric acid prior to treatment with said microorganism.

* * * * *